(12) United States Patent
Bi

(10) Patent No.: US 7,845,212 B1
(45) Date of Patent: Dec. 7, 2010

(54) HIGH PRESSURE HIGH TEMPERATURE SAGGING TESTER

(75) Inventor: Hongfeng Bi, 3722 Shadow Wick Ln, Houston, TX (US) 77082

(73) Assignee: Hongfeng Bi, Houston, TX (US)

( * ) Notice: Subject to any disclaimer, the term of this patent is extended or adjusted under 35 U.S.C. 154(b) by 459 days.

(21) Appl. No.: 12/075,371

(22) Filed: Mar. 11, 2008

(51) Int. Cl.
  *G01N 33/18* (2006.01)
  *G01N 3/02* (2006.01)
(52) U.S. Cl. .................... 73/61.63; 73/865.6
(58) Field of Classification Search ............. 73/61.63, 73/865.6
See application file for complete search history.

(56) References Cited

U.S. PATENT DOCUMENTS

| | | | |
|---|---|---|---|
| 2,845,793 A | 8/1958 | Cardwell, Jr. | |
| 3,289,467 A | 12/1966 | Parker et al. | |
| 3,371,523 A | 3/1968 | Crouch et al. | |
| 3,744,633 A | 7/1973 | Schmidt, Jr. et al. | |
| 4,474,056 A | 10/1984 | O'Brien et al. | |
| 5,086,646 A | 2/1992 | Jamison et al. | |
| 5,987,969 A | 11/1999 | Joseph et al. | |
| 6,240,770 B1 * | 6/2001 | Raffer | 73/54.28 |
| 6,330,826 B1 * | 12/2001 | Meeten | 73/152.62 |
| 6,584,833 B1 * | 7/2003 | Jamison et al. | 73/61.63 |

\* cited by examiner

*Primary Examiner*—Hezron Williams
*Assistant Examiner*—Nathaniel Kolb

(57) ABSTRACT

A method and apparatus for analyzing sag in drilling fluids or solid bearing fluids wherein a cylindrical high-pressure cell assembly (80) capable of withstanding high pressure and high temperature with a coaxial cylindrical rotor (33) driven to rotate inside cell assembly (80), a sample port (12) for testing sample subtraction used for further analysis, and a sample inlet port (74) for adding testing sample. This said cell assembly (80) is supported on a pivotal cell support (90) so that it can be tilted and fixed at any angle.

20 Claims, 5 Drawing Sheets

HIGH PRESSURE HIGH TEMPERATURE SAGGING TESTER

CROSS-REFERENCE TO RELATED APPLICATIONS

None.

BACKGROUND

1. Field of Invention

The present invention relates to apparatuses and methods for monitoring, measuring, or analyzing the sag of a weighted material in a drilling fluid.

2. Description of Prior Art

This tester applies to "sagging" of oil well fluids. Sagging is the settling of weighted additives in the wellbore during drilling conditions, as well as times of static activity. This directly applies to dense materials, such as Barite, used in the drilling fluid. These materials serve little purpose other than a weighting agent. The density measurement is the focus of this tester.

Settling or sag is not an issue with vertical or near vertical drilling, but problematic with higher drilling angles. As these modern angles increase, sag becomes more of an obstacle. Sagging can reduce the rate of penetration, fluid flow, and cutting removal. Sag can occur when the flow of the fluid ceases, as when the drill string stops. Sag can also concentrate in one area during this "static" time.

Addressing this concern has been an issue since the 1920s. Many adjustments to fluids have been made in an effort to alleviate this problem. Until now, minimal substantial test data were available for such research. Drilling fluid changes were made based upon guesswork in the field in the past. Data supporting downhole mud density is critical for modern production and performance.

A few types of arrangements have been applied to measure the sag of drilling fluids. In U.S. Pat. No. 6,330,826, an apparatus consists of a conically or frustro-conically shaped inner body; an outer body having an opening with contours closely matching those of inner body such that in conjunction inner and outer body are separated by an arrow gap defining a conically or fustro-conically volume with a vertex; a motor drive for rotating the inner body with respect to the outer body; and a sampling access to determine the density of said drilling fluid with a localized part of said volume. One of the drawbacks of this setup is that it can not simulate downhole mud conditions which are under high pressure and high temperature. One other drawback of this apparatus is that the inner and outer body shapes are considerably different from the real drilling conditions in which both bore hole and drilling pipe are cylindrical. In U.S. Pat. No. 6,584,833, a device was disclosed for measuring dynamic and static sag of drilling fluids under high temperature and high pressure conditions. One of the drawbacks of this invention is its complexity. It consists of a very complicated testing cell and delicate electronics and control systems. As of 2007, its cost to build is about 8 times of the current invention. Another drawback of this invention is that it is difficult to achieve more than 5,000 psi due to the nature of its design. Because it needs to sense tiny shifts of center of gravity, it can not use a heavy high-pressure vessel. The current invention can easily test samples up to or more than 30,000 psi. Another drawback of this invention is that it is very difficult to operate and difficult to clean due to its many components and complex design.

It is an object of this invention to provide a sag tester wherein dynamic and static sag caused by settling of weighting materials in drilling fluids or other solids bearing fluids can be accurately determined under conditions closely simulating down-hole environments.

It is another object of this invention to provide a sag tester wherein dynamic and static sag of weighting materials in drilling fluids or other solids bearing fluids can be accurately determined under any inclined angle which simulates any high or low angle drilling operation.

It is another object of this invention to provide a sag tester that requires substantially less maintenance work yet meets industry standards of accuracy, reliability, durability, dependability, and ease of cleaning.

SUMMARY

A sagging tester in accord with the present invention conveniently comprises of a cylindrical high-pressure vessel capable of withstanding high pressure and high temperature with a coaxial cylindrical rotor assembly located inside, which could be driven to rotate through an outside magnetic coupling. One testing sample addition port and at least one testing sample extraction port are attached to the high-pressure vessel for pressure maintenance and testing sample subtraction. Density changes, composition and other properties of subtracted samples can be obtained with a density meter, pycnometer, fluid analyzer, etc.

The apparatus and method of the present invention provide an alternative way to measure or analyze dynamic and static sag caused by settling of weighting materials in drilling fluids or other solids bearing fluids under high-pressure high-temperature conditions. It can also measure the viscosity of a testing fluid in addition to measuring weighted material sagging.

DRAWING FIGURES

Other objects, features and advantages will be apparent from the following detailed description of preferred embodiments taken in conjunction with accompanying drawing in which.

Figure 1:
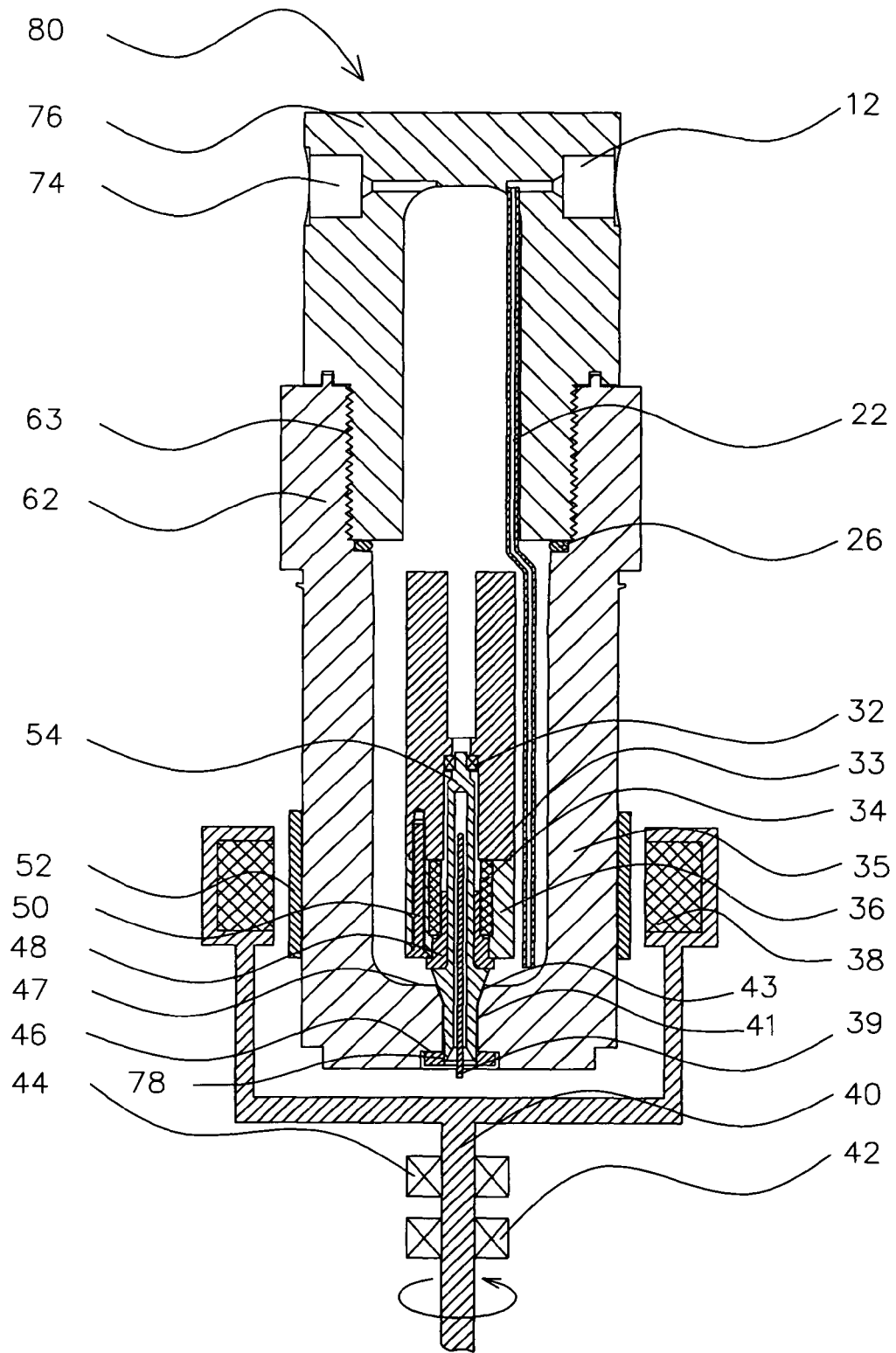
FIG. 1 is a cross-section view of the cell assembly 80 in preferred embodiment of the invention.

| Reference Numerals in Drawings | |
|---|---|
| 12 | sample port |
| 12A | sample port |
| 12B | sample port |
| 22 | sampling tube |
| 26 | o-ring |
| 26A | o-ring |
| 27A | piston |
| 28A | o-ring |
| 30A | screw thread |
| 32 | support bearing |
| 33 | rotor |
| 33A | inside rotor |
| 34 | coupling magnet |
| 35 | cell wall |
| 35A | cell wall |
| 36 | magnet holder |

-continued

| Reference Numerals in Drawings | |
|---|---|
| 37A | dynamic seal |
| 38 | driving-magnet |
| 39 | thermal couple |
| 39A | thermal couple |
| 40 | magnet mount |
| 41 | straight bore |
| 41A | thermal couple port |
| 42 | bearing |
| 43 | conical surface |
| 44 | bearing |
| 45A | shaft |
| 46 | lock nut |
| 47 | cell bottom |
| 47A | cell bottom |
| 48 | bushing |
| 49A | motor |
| 50 | screw |
| 52 | heater |
| 52A | heater |
| 54 | pivot |
| 62 | cell body |
| 62A | cell body |
| 63 | screw thread |
| 63A | screw thread |
| 74 | sample inlet port |
| 74A | pressurization port |
| 76 | cell cap |
| 76A | cell cap |
| 78 | thread |
| 80 | cell assembly |
| 80A | cell assembly |
| 80B | cell assembly |
| 90 | cell support |
| 90A | cell support |
| 90B | cell support |
| 92 | piston |
| 92B | piston |
| 94 | pressurization oil chamber |
| 94B | pressurization oil chamber |
| 96 | liquid pump |
| 96A | liquid pump |
| 96B | liquid pump |
| 98 | sample reservoir |
| 100 | relief valve |
| 100A | relief valve |
| 100B | relief valve |
| 102 | sample chamber |
| 102B | sample chamber |
| 104 | sampling valve |
| 104A | sampling valve |
| 104B | 3-way valve |
| 106 | high pressure sample vessel |
| 106A | high pressure sample vessel |
| 106B | high pressure sample vessel |

DESCRIPTION

Figure 2:
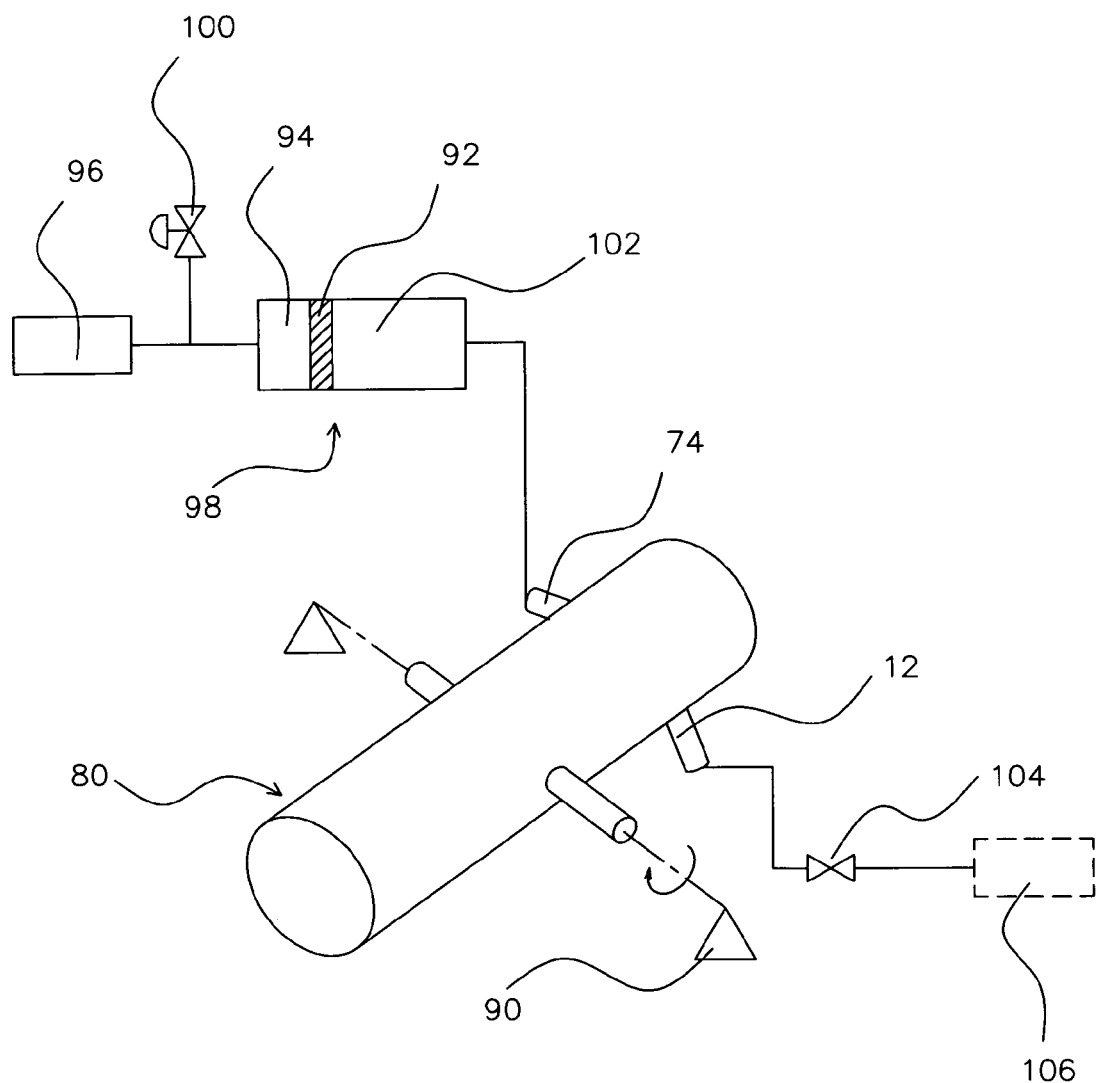
FIG. 2 is the flow diagram of this invention.

FIGS. 1 and 2—Preferred Embodiment

FIG. 1, is a cross-section view of a cell assembly 80 with a cell body 62 and a cell cap 76. Cell body 62 is detachable from cell cap 76 via a screw thread 63. An o-ring 26 assures against the escape of fluid through screw thread 63. Inside of cell body 62 and below screw thread 63 is a cylindrical cell wall 35, which extends downward to a cell bottom 47. A tapered hole with a conical surface 43 and a straight bore 41 is located in the center of cell bottom 47. A pivot 54, which is secured to cell bottom 47 by a lock nut 46 through a thread 78, is seated into said tapered hole on conical surface 43. Lock nut 46 is tightened to provide initial seal on conical surface 43 between cell bottom 47 and pivot 54. A thermal couple 39 is inserted into the center of pivot 54. Radially outward of the outer surface of pivot 54 is a bushing 48. Bushing 48 is made of Rulon, Teflon or equivalent plastics. A magnet holder 36 and a coupling magnet 34 are positioned radially outward of bushing 48. A screw 50 secures magnet holder 36 and coupling magnet 34 to the bottom of a rotor 33. A support bearing 32 provides vertical support of the assembly of rotor 33, magnet holder 36 and coupling magnet 34, which can rotate freely on the same central axis of pivot 54. A sample inlet port 74 is provided to maintain the inside pressure of cell assembly 80 at a constant value. Sample can be added or bleed off from sample inlet port 74. A sample port 12 is also provided just to subtract sample from cell assembly 80 for measurement and analysis. A sampling tube 22 connects to the end of sample port 12 tightly and their connection is sealed from the sample at the top of cell assembly 80. The other end of sampling tube 22 extends to the bottom of cell assembly 80. This ensures that the sample subtracted from cell assembly 80 is from its bottom. A magnet mount 40 is rotationally supported on the outside of cell body 62 by a bearing 42 and a bearing 44. Magnet mount 40 can be rotated by any conventionally means such as gearbox or motor. A driving magnet 38 is mounted on magnet mount 40 at approximately the same level where coupling magnet 34 is mounted inside of the cell body 62. In FIG. 2, Cell assembly 80 is supported on a cell support 90 and can be tilted and fixed at any inclined positions from 0 to 90 degree corresponding to the horizontal plane. A sample reservoir 98 is connected to sample inlet port 74. A pressurization oil chamber 94 and a sample chamber 102 are inside of sample reservoir 98 and are separated by a piston 92. Piston 92 effectively prevents the mixing between pressurization fluid and testing sample. A relief valve 100 and a liquid pump 96 are both connected to sample reservoir 98 at pressurization oil chamber 94 side. A sampling valve 104 connects to sample port 12. High pressure sample vessel 106 is optional and is connected to sampling valve 104.

OPERATION

FIGS. 1 and 2—Preferred Embodiment

In FIG. 1, Pivot 54 is secured to cell body 62 by lock nut 46 and can be cleaned together with cell body 62. During installation, screw 50 holds magnet holder 36, coupling magnet 34 and rotor 33 together. Bushing 48 is pushed into the bottom of magnet holder 36. This said subassembly is dropped into cell body 62 and rotationally supported by pivot 54. A motor or gearbox drives magnet mount 40 to rotate carrying driving magnet 38. Due to the magnetic coupling between driving magnet 38 and coupling magnet 34, rotor 33 rotates at the same revolving speed as magnet mount 40 does. Test sample is poured into cell body 62 so that sample surface submerges the top of rotor 33. Screw down cell cap 76 with o-ring 26 in place. Add more test sample fluid from sample port 12 until sample starts to come out from sample inlet port 74 in order to expel all air inside of cell assembly 80. A heater 52 heats up cell body 62 while thermal couple 39 provides temperature feedback for temperature control. In FIG. 2, cell assembly 80 is then mounted on cell support 90 and is tilted to desired angle. Relief valve 100 and sample valve 104 are turned off. Next, liquid pump 96 starts to pump pressurization oil to pressurization oil chamber 94 inside of sample reservoir 98. Piston 92 is moved by pressurization oil and pushes more testing sample inside of sample chamber 102 into cell assembly 80 through sample inlet port 74. After desired pressure is reached, pump 96 is turned off. Magnet mount 40 is driven to rotate at desired speed and heater 52 heats up cell assembly 80 to desired temperature. If the pressure inside of cell assembly 80 is above desired pressure, relief valve 100 will be turned on briefly to bleed off small amount of pressurization oil until the pressure inside of cell assembly 80 is dropped back to desired value.

After a desired duration of time, sampling valve 104 is opened. High pressure sample vessel 106 is to receive sample under high temperature and high pressure conditions and to cool the sample off before discharging to atmospheric environment. High pressure sample vessel 106 is optional since sample can be directly discharged to atmospheric environment if evaporation of sample is not an issue. Because of sampling tube 22 of FIG. 1, the sample withdrawn from cell assembly 80 is near the bottom of cell assembly 80. This discharged sample is further analyzed for its composition and its density is measured. At last, tested sample sagging information is derived from those data.

While subtracting sample from cell assembly 80, liquid pump 96 pumps more pressurization fluid into sample reservoir 98 which in turn adds more sample to cell assembly 80 to maintain the inside pressure of cell assembly 80.

In FIG. 1, viscosity of tested sample at an elevated temperature and pressure condition is also obtained by measuring the power consumption of the driving device that keeps driving magnet 38 rotating at a constant speed. Because cell wall 35 is static and rotor 33 is rotating, there is a drag due to the viscosity of the tested sample applied on the outside surface of rotor 33. At a constant rotating speed, a thicker tested sample causes more drag on the outside surface of rotor 33. Thus, more energy is consumed in the driving device to overcome this drag.

DESCRIPTION

Figure 3:
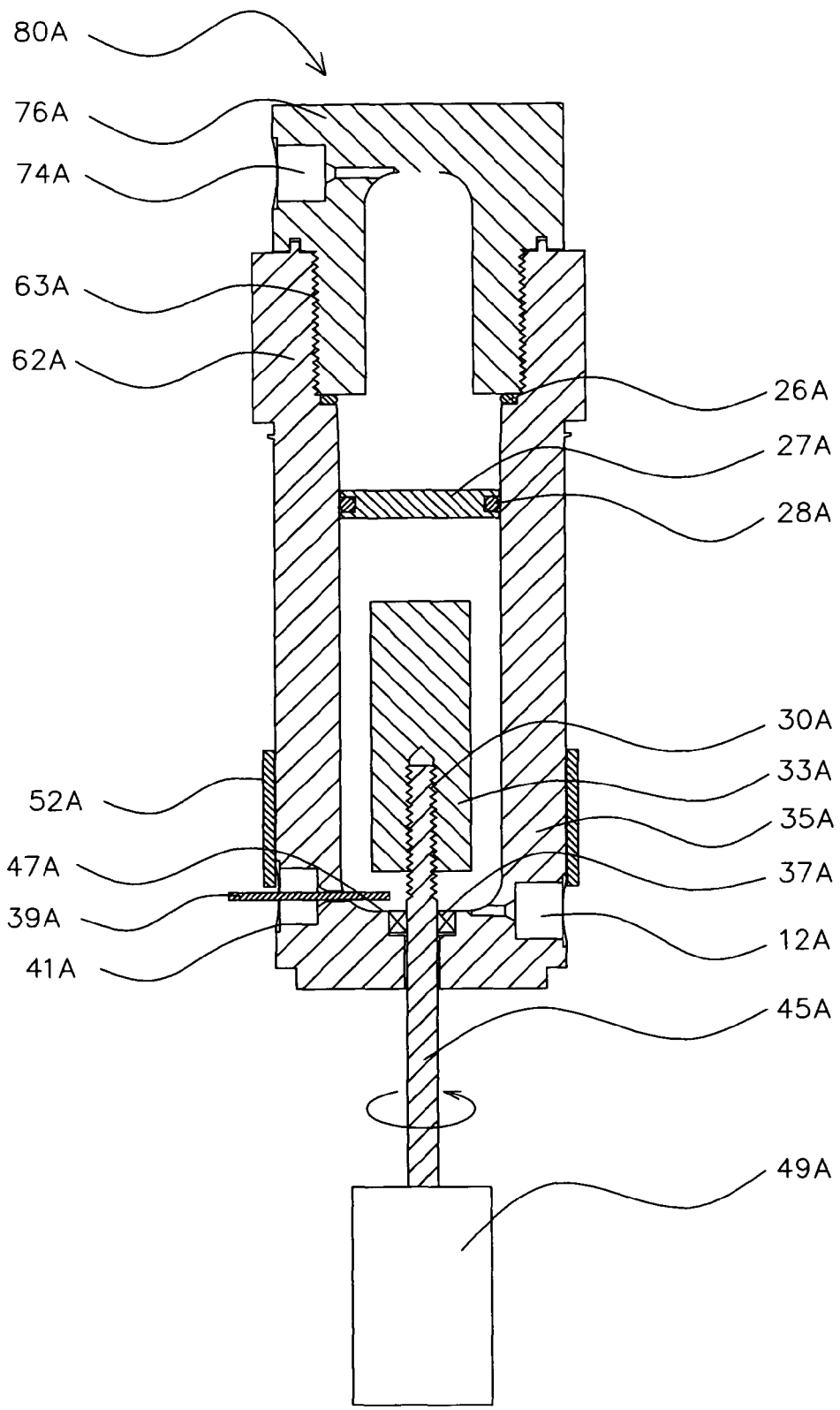
FIG. 3 shows an alternative configuration of cell assembly 80A.
Figure 4:
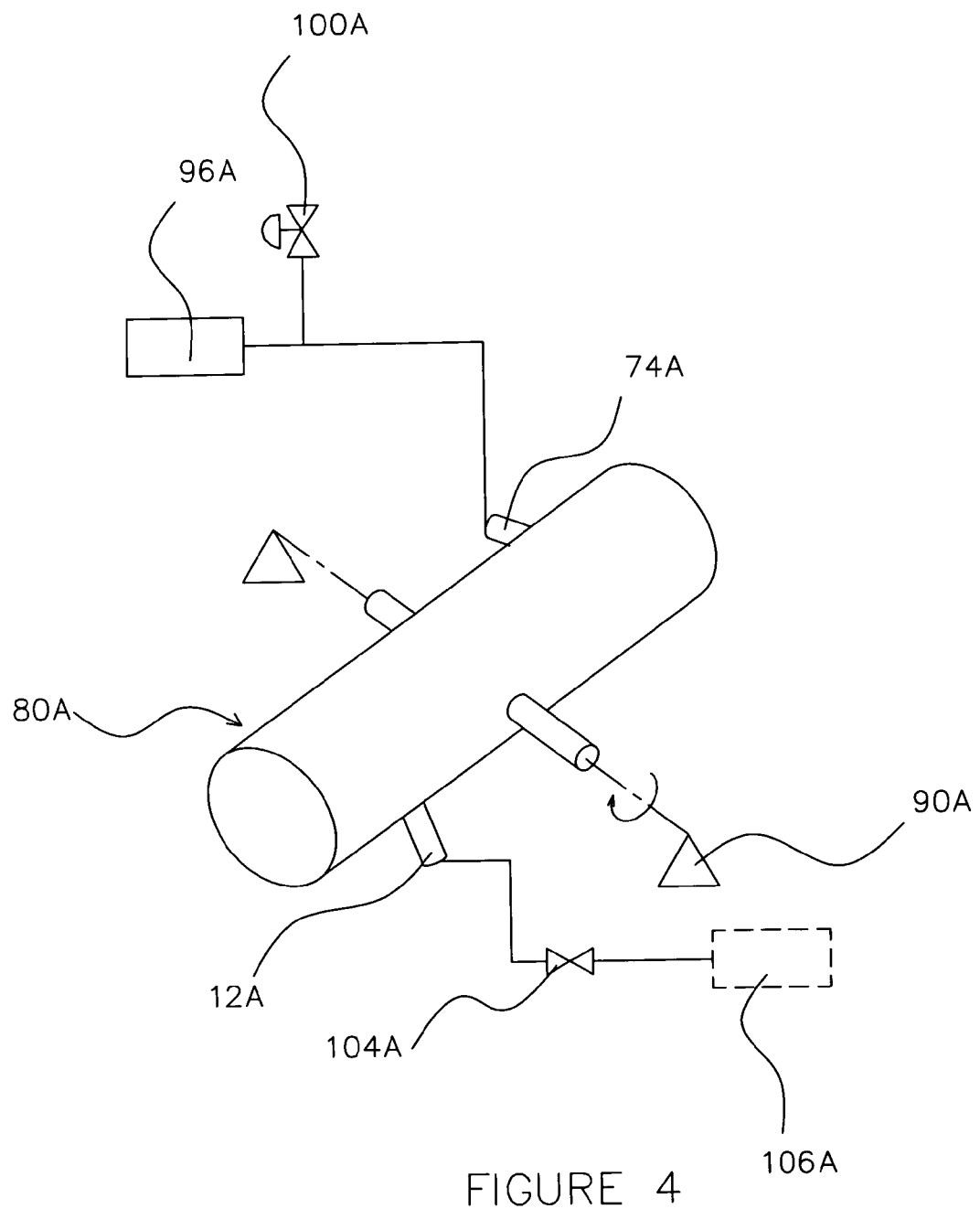
FIG. 4 is the flow diagram with an alternative cell assembly 80A.

FIGS. 3 and 4—An Alternative Cell Assembly Embodiment with Different Sample Withdrawn Configuration FIG. 3 shows a cross-section view of a cell assembly 80A with a different sample withdrawn configuration. Cell assembly 80A consists of a cell body 62A and a cell cap 76A. Cell body 62A is detachable from cell cap 76A via a screw thread 63A. An o-ring 26A assures against the escape of fluid through screw thread 63A. Inside of cell body 62A and below screw thread 63A is a cylindrical cell wall 35A that extends downward to a cell bottom 47A. A shaft 45A driven by a motor 49A inserts into the bottom of cell assembly 80A. An inside rotor 33A connects to the top of shaft 45A through a screw thread 30A. Inside rotor 33A is cylindrical shape and located approximately in the center of cell body 62A. A dynamic seal 37A provides seal between cell bottom 47A and shaft 45A. A thermal couple 39A is inserted into the bottom of cell assembly 80A through a thermal couple port 41A. A pressurization port 74A is provided to maintain the inside pressure of cell assembly 80A at a constant value. Sample can be added or bled off from pressurization port 74A. A sample port 12A is also provided just to subtract sample from cell assembly 80A for measurement and analysis. Sample port 12A is located considerably at the lower portion of cell body 62A and connects to cell bottom 47A in radial direction. This ensures that the sample subtracted from cell assembly 80A is from its bottom. A piston 27A is located inside of cell body 62A. Below piston 27A is filled with testing sample and above piston 27A is filled with pressurization fluid. An o-ring 28A provides the seal between testing sample and pressurization fluid. In FIG. 2, Cell assembly 80A is supported on a cell support 90A and can be tilted at any inclined positions from 0 to 90 degree corresponding to the horizontal plane. A relief valve 100A and a liquid pump 96A are both connected to pressurization port 74A. A sampling valve 104A connects to sample port 12A. High pressure sample vessel 106A is optional and is connected to sampling valve 104A.

OPERATION

FIGS. 3 and 4—An Alternative Cell Embodiment with Different Sample Withdrawn Configuration In FIG. 3, Shaft 45A sticks into the bottom of cell body 62A. Then screw inside rotor 33A to the end of shaft 45A. Pour predetermined amount of testing sample into cell body 62A. Insert piston 27A. Add some pressurization fluid on top of piston 27A. Screw down cell cap 76A with o-ring 26A in place. More pressurization fluid can be added from pressurization port 74A. A heater 52A heats up cell body 62A while thermal couple 39A provides temperature feedback for temperature control. In FIG. 4, cell assembly 80A is then mounted on cell support 90A and is tilted to desired angle. Relief valve 100A and sample valve 104A are turned off. Next, liquid pump 96A starts to pump pressurization oil to cell assembly 80A. After desired pressure is reached, pump 96A is turned off. Motor 49A drives inside rotor 33A to rotate at desired speed and heat 52A heats up cell assembly 80A to desired temperature. If the pressure inside of cell assembly 80A is above desired pressure, relief valve 100A will be turned on briefly to bleed off small amount of pressurization oil until the pressure inside of cell assembly 80A is dropped back to desired value.

In FIG. 4, After a desired duration of time, sampling valve 104A is opened. High pressure sample vessel 106A is to receive sample under high temperature and high pressure conditions and to cool the sample off before discharging to atmospheric environment. High pressure sample vessel 106A is optional since sample can be directly discharged to atmospheric environment if evaporation of sample is not an issue. This discharged sample is further analyzed for its composition and its density is measured. At last, tested sample sagging information is derived from those data. While subtracting sample from cell assembly 80A, liquid pump 96A pumps more pressurization fluid into cell assembly 80A to maintain the inside pressure of cell assembly 80A.

In FIG. 3, viscosity of tested sample at an elevated temperature and pressure condition is also obtained by measuring the power consumption of motor 49A. Because cell wall 35A is static and inside rotor 33A is rotating, there is a drag due to the viscosity of the tested sample applied on the outside surface of inside rotor 33A. At a constant rotating speed, a thicker tested sample causes more drag on the outside surface of rotor 33A. Thus, more energy is consumed in motor 49A to overcome this drag.

DESCRIPTION

Figure 5:
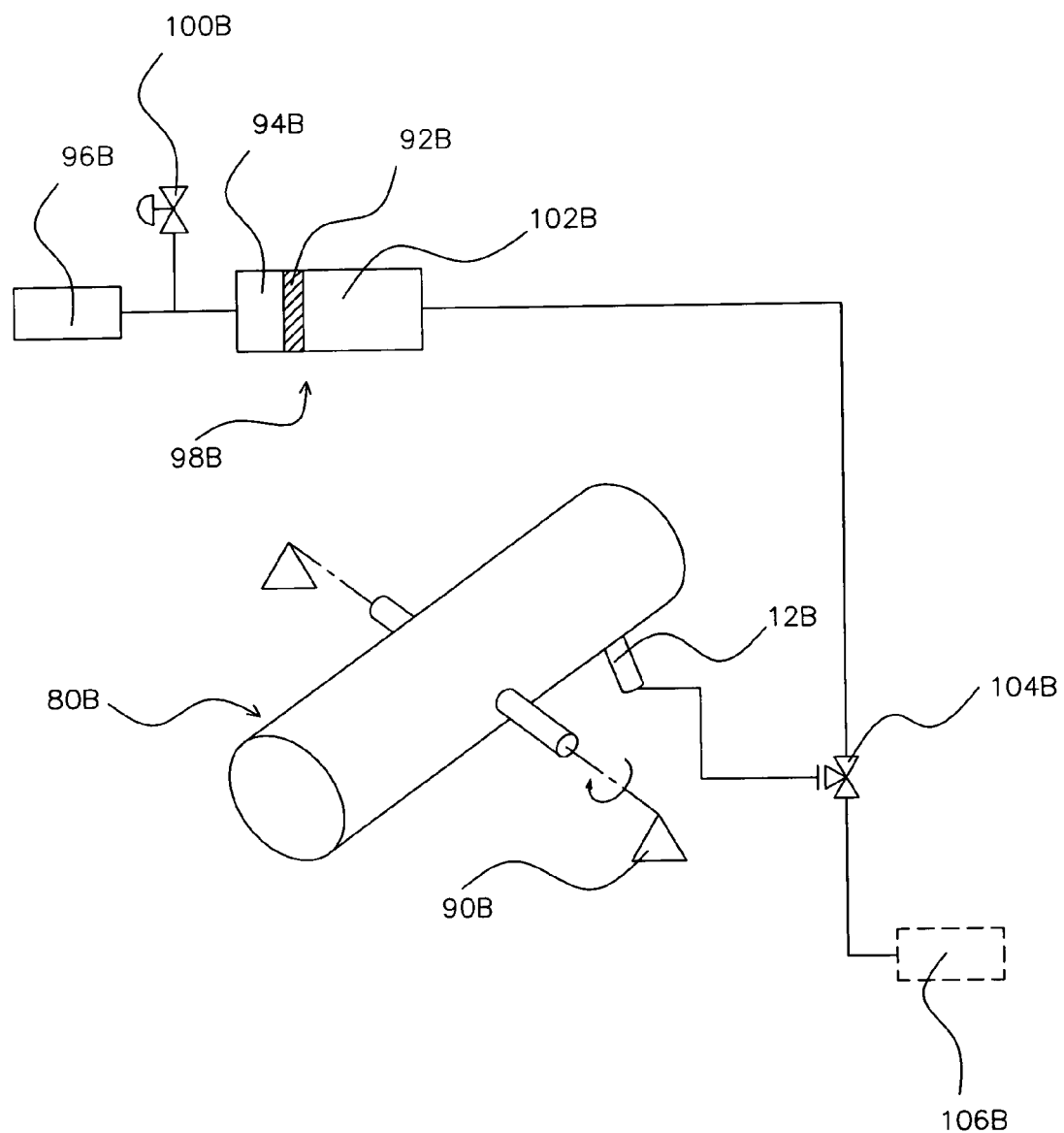
FIG. 5 shows a flow diagram with another alternative cell assembly 80B with just one port.

FIG. 5—An Alternative Configuration with Only One Port on Pressure Cell Assembly In FIG. 5, a cell assembly 80B is supported on a cell support 90B and can be tilted and fixed at any inclined positions from 0 to 90 degree corresponding to the horizontal plane. Cell assembly 80B has similar inside configuration compared to cell assembly 80 in FIG. 1, except it does not have a designated sample inlet port as sample inlet port 74 in FIG. 1. A sample reservoir 98B is connected to a 3-way valve 104B. A pressurization oil chamber 94B and a sample chamber 102B are inside of sample reservoir 98B and are separated by a piston 92B. Piston 92B effectively prevents the mixing between pressurization fluid and testing sample. A relief valve 100B and a liquid pump 96B are both connected to sample reservoir 98B at pressurization oil chamber 94B side. 3-way valve 104B connects to a sample port 12B on cell assembly 80B. High pressure sample vessel 106B is optional and is connected to 3-way valve 104B.

OPERATION

FIG. 5—An Alternative Configuration with Only One Port on Pressure Cell Assembly In FIG. 5, cell assembly 80B is then mounted on cell support 90B and is tilted to desired angle. Relief valve 100B is turned off. 3-way valve 104B is set to connect sample port 12B to sample reservoir 98B. Next, liquid pump 96B starts to pump pressurization oil to pressurization oil chamber 94B inside of sample reservoir 98B. Piston 92B is moved by pressurization oil and pushes more testing sample inside of sample chamber 102B into cell assembly 80B through sample port 12B. After desired pressure is reached, pump 96B is turned off. If the pressure inside of cell assembly 80B is above desired pressure, relief valve 100B will be turned on briefly to bleed off small amount of pressurization oil until the pressure inside of cell assembly 80B is dropped back to desired value.

After a desired duration of time, 3-way valve 104B is switched to connect sample port 12B to high pressure sample vessel 106B. High pressure sample vessel 106B is to receive sample under high temperature and high pressure conditions and to cool the sample off before discharging to atmospheric environment. High pressure sample vessel 106B is optional since sample can be directly discharged to atmospheric environment if evaporation of sample is not an issue. This discharged sample is further analyzed for its composition and its density is measured. At last, tested sample sagging information is derived from those data.

Ramifications

Rotor 33 and inside rotor 33A do not have to be cylindrically shaped. They could be a blade, frame or any geometry shape. Furthermore, rotor 33 and inside rotor 33A could be eliminated if shearing of fluid is not required.

In FIG. 1, multiple sample ports which are similar to sample port 12 can be provided along with sampling tubes which are similar to sampling tube 22 with their ends at different locations with cell assembly 80. With this arrangement, samples at various height of cell assembly 80 can be subtracted at relatively the same time. Thus, the distribution of density inside of cell assembly 80 can be obtained.

Cell wall 35 in FIG. 1 and cell wall 35A in FIG. 3 could be conical shape instead of cylindrical.

Testing sample subtracted from the bottom of cell assembly 80 could also be analyzed for other properties besides density.

In FIG. 1, driving magnet 38 could be driven to rotate in an oscillatory fashion as well instead of just constant direction, while power consumption of driving device is monitored. Similarly, in FIG. 3, insider rotor 33A could be driven to rotate in an oscillatory fashion instead of just constant direction, while power consumption of motor 49A is monitored. Thus visco-elasticity of tested sample could be obtained as well.

In FIG. 1, the end of sample tube 22 does not have to be located at the bottom of cell assembly 80. The end of sample tube 22 could be located at any height to study the density change over time at that particular location. Similarly the breakthrough point of port 12A into cell assembly 80A in FIG. 3 does not have to be located at the bottom of cell assembly 80A.

In FIG. 2, sample reservoir 98 does not have to be a piston style. It could be a bladder type accumulator or anything equivalent.

In FIG. 2, once sample is withdrawn and shut in high pressure sample vessel 106, total weight of high pressure sample vessel 106 could be measured to calculate the density of testing sample without have to discharge it out.

In FIG. 1, driving magnet 38 does not have to be located radially outside of cell assembly 80. It could locate beneath of cell assembly 80 as long as it can generate a magnetic coupling with coupling magnet 34.

In FIG. 2, besides density, other properties of extracted sample in high pressure sample vessel 106 from cell assembly 80 could be measured with other kind of equipment to determine the sagging of drilling fluids as well.

In FIG. 3, piston 27A can be removed if mixing between pressurization fluid and testing sample would not be a problem or liquid pump 96A in FIG. 4 can pump testing sample directly.

Conclusion, and Scope

Accordingly, the reader will see that this invention can be used to construct a pivotal high pressure vessel from which sample can be subtracted under high pressure and high temperature conditions for density change monitoring. This said structure could also provide shear to testing sample at a desired rate. It satisfies an eminent drilling industry need.

Objects and Advantages

From the description above, a number of advantages of my sagging tester become evident:

(a) Drilling fluids under high temperature and high pressure can be subtracted from high pressure testing vessel for density and other analysis without reducing the pressure inside of testing vessel.

(b) Due to limited number of components, current invention is easy to operate and maintain.

(c) The pressure rating of current invention will only be limited to the pressure rating of its pressure vessel, tubing and valves, which can be up to 60,000 psi. Previously no sag information of drilling fluids has been obtained under more than 5,000 psi pressure conditions.

(d) Current invention can test drilling fluids dynamically and statically under high pressure, high temperature and various inclined positions.

Further objects and advantages of my invention will become apparent from a consideration of the drawings and ensuing description.

The invention claimed is:

1. A sagging tester comprising:
(a) a pressure vessel rated for at least 200 psi and above,
(b) a rotor within said pressure vessel which is driven to rotate while contacting with a sample liquid to be measured,
(c) means for driving said rotor to rotate,
(d) at least one opening on said pressure vessel from which some of said sample liquid can be extracted from said pressure vessel due to pressure difference,
(e) means for measuring at least one sagging related property of said sample liquid extracted from said pressure vessel,
(f) means for maintaining the inside pressure of said pressure vessel constant, wherein said means for maintaining the inside pressure comprise a pressure port from which more fluid can be added into said pressure vessel to maintain the inside pressure of said pressure vessel.

2. The sagging tester of claim 1 wherein said means for measuring at least one sagging related property of said sample liquid is a density measurement device.

3. The sagging tester of claim 1 wherein said means for driving said rotor to rotate is a magnetic coupling across said pressure vessel wall.

4. The sagging tester of claim 1 wherein said means for driving said rotor to rotate is a motor.

5. The sagging tester of claim 1 wherein said rotor is of a cylindrical shape.

6. The sagging tester of claim 1 wherein said rotor is a stirring blade.

7. The sagging tester of claim 1 further comprising means for measuring the power consumption of said means for driving said rotor to rotate.

8. The sagging tester of claim 1 further comprising a tube with its one end connected to said opening on said pressure vessel and with its other end at a desired location inside of said pressure vessel.

9. The sagging tester of claim 8 wherein said desired location is the bottom of said pressure vessel.

10. The sagging tester of claim 1 further comprising a pivot support, which can support said pressure vessel at any inclined position.

11. A sagging tester comprising:
    (a) a pressure vessel with a sample liquid to be measured inside,
    (b) a pivot support, which can support said pressure vessel at any inclined position,
    (c) a sample port on said pressure vessel from which some of said sample liquid can be extracted from said pressure vessel due to pressure difference,
    (d) a pressure port on said pressure vessel from which more fluid can be added into said pressure vessel to maintain the inside pressure of said pressure vessel constant,
    (e) means for measuring at least one sagging related property of said sample liquid extracted from said pressure vessel.

12. The sagging tester of claim 11 wherein said means for measuring at least one sagging related property of said sample liquid is a density measurement device.

13. The sagging tester of claim 11 further comprising a tube with its one end connected to said sample port and with its other end at a desired location inside of said pressure vessel.

14. The sagging tester of claim 13 wherein said desired location is the bottom of said pressure vessel.

15. The sagging tester of claim 11 further comprising means to separate said sample liquid from a pressurization fluid which is used to pressurize said pressure vessel.

16. The sagging tester of claim 15 wherein said means to separate said sample liquid from said pressurization fluid is a piston.

17. A sagging tester comprising:
    (a) a pressure vessel,
    (b) a pivotal support which can support said pressure vessel at any inclined angle;
    (c) a rotor within said pressure vessel which is driven to rotate while contacting with a sample liquid to be measured,
    (d) means for driving said rotor to rotate,
    (e) at least one opening on said pressure vessel from which some of said sample liquid can be extracted from said pressure vessel due to pressure difference,
    (f) a sample reservoir from which more sample can be added to said pressure vessel,
    (g) means for measuring at least one sagging related property of said sample liquid extracted from said pressure vessel,
    (h) a pressure port on said pressure vessel from which more fluid can be added into said pressure vessel to maintain the inside pressure of said pressure vessel constant.

18. The sagging tester of claim 17 wherein said means for measuring at least one property of said sample liquid is a density measurement device.

19. The sagging tester of claim 17 wherein said means for driving said rotor to rotate is a magnetic coupling across said pressure vessel wall.

20. The sagging tester of claim 17 further comprising a tube with its one end connected to said opening on said pressure vessel and with its other end at a desired location inside of said pressure vessel.

* * * * *